United States Patent [19]
Brown et al.

[11] Patent Number: 5,631,387
[45] Date of Patent: May 20, 1997

[54] PROCESS FOR THE PREPARATION AND RECOVERY OF MALEIC ANHYDRIDE

[75] Inventors: Henry C. Brown; William H. Alumbaugh, both of Pensacola, Fla.

[73] Assignee: Huntsman Petrochemical Corporation, Salt Lake City, Utah

[21] Appl. No.: 406,674

[22] Filed: Mar. 20, 1995

[51] Int. Cl.$^6$ ............................................. C07D 307/60
[52] U.S. Cl. ..................... 549/259; 549/256; 549/258; 549/262
[58] Field of Search ...................... 549/256, 258, 549/259, 262

[56] References Cited

U.S. PATENT DOCUMENTS

| | | | |
|---|---|---|---|
| 4,111,963 | 9/1978 | Mount et al. | 260/346.75 |
| 4,118,403 | 10/1978 | White | 549/262 |
| 4,456,764 | 6/1984 | Wrobleski | 549/260 |
| 4,515,973 | 5/1985 | Wrobleski | 549/259 |

OTHER PUBLICATIONS

"Chemical and Process Technology Encyclopedia", 1974, pp. 714–716.

*Primary Examiner*—Bernard Dentz
*Attorney, Agent, or Firm*—Senniger, Powers, Leavitt & Roedel

[57] ABSTRACT

An improved process for the preparation and recovery of maleic anhydride in which the recovery of maleic anhydride from a gaseous reaction mixture includes absorbing the maleic anhydride in a solvent and subsequently stripping maleic anhydride from the solvent to obtain crude maleic anhydride product and regenerated absorbing solvent containing polymeric tars and other contaminants. In accordance with the improvement, at least a portion of the regenerated solvent is contacted in an agitated extraction zone with an aqueous liquid extractant to hydrolyze the polymeric tars, transfer water-soluble contaminants to the aqueous extract phase and produce a mixture comprising an aqueous extract phase containing water-soluble contaminants and an organic raffinate phase comprising regenerated absorbing solvent having a reduced concentration of polymeric tars. The aqueous extract and organic raffinate phases are then separated and the organic phase is recycled and used again to absorb maleic anhydride.

21 Claims, 1 Drawing Sheet

FIG. 1

PROCESS FOR THE PREPARATION AND RECOVERY OF MALEIC ANHYDRIDE

BACKGROUND OF THE INVENTION

The present invention relates to the preparation and recovery of maleic anhydride. More particularly, the present invention is directed to improvements in processes and apparatus for the preparation of maleic anhydride in which the recovery of maleic anhydride from a gaseous reaction mixture includes absorbing the maleic anhydride in a solvent, and subsequently stripping maleic anhydride from the solvent to obtain crude maleic anhydride product.

Maleic anhydride is used alone or in combination with other acids in the manufacture of alkyd and polyester resins. It is also a versatile intermediate for chemical synthesis.

Maleic anhydride is prepared commercially by contacting a feed gas comprising molecular oxygen and a suitable hydrocarbon (e.g., n-butane or butene) with a vanadium-phosphorus-oxygen catalyst to partially oxidize the hydrocarbon and produce maleic anhydride. Hydrocarbons are converted to maleic anhydride by passing the feed gas through a tubular reactor containing a fixed bed of catalyst. The reaction product gas which is produced contains maleic anhydride together with oxidation by-products such as CO, $CO_2$, water vapor, acrylic and acetic acids and other by-products, along with inert gases present in air when air is used as the source of molecular oxygen.

The prior art discloses a number of methods of isolating and recovering maleic anhydride from the reaction product gas. For example, the maleic anhydride can be recovered by direct condensation from the reaction product gas or by scrubbing the gas with water and dehydrating the resulting aqueous mixture by azeotropic distillation with xylene. However, due to increased product yields, the preferred method of recovery comprises selectively absorbing the maleic anhydride in a suitable solvent and subsequently stripping the maleic anhydride from the resulting absorption liquor to obtain crude product. U.S. Pat. No. 4,118,403 (White) discloses contacting the reaction product gas with an organic solvent in an absorber column so that the maleic anhydride, as well as some of the oxidation by-products, are absorbed in the solvent. The solvent comprises a dialkyl phthalate having 2 to 8 carbon atoms in each alkyl chain (e.g., dibutyl phthalate), and from about 0.5 to about 10 weight percent phthalic anhydride. Maleic anhydride is isolated from the rich absorbing liquor by stripping the liquor in a single step stripping operation. The solvent which has been stripped of maleic anhydride is then cooled and circulated back to the absorber.

Although processes like that disclosed by White have proven to be satisfactory in recovering maleic anhydride in high yields, prior art methods of this type have several disadvantages. By-products of the partial oxidation reaction such as acrylic acid tend to accumulate in the circulating absorbing solvent, along with other contaminants such as maleic, fumaric and phthalic acids, phthalic anhydride and polymeric tars formed in the absorption and stripping loop. The polymeric tars contain anhydride, acid and ester units and, during steady state operation, have an average molecular weight of about 30,000. The accumulated contaminants, especially the tars, cause plugging and fouling of the process equipment (e.g., heat transfer surfaces), and may have an adverse impact on maleic anhydride quality. Moreover, tar generation reactions tend to be autocatalytic, so that accumulation of the tars may also have an adverse effect on yields.

In order to prevent the build-up of contaminants, White discloses filtering the absorbing solvent after it has been stripped of maleic anhydride to remove fumaric acid. White also teaches distilling a slip stream of the stripped solvent to remove soluble tars. The filtered solvent and the distilled solvent are then recombined and recycled to the absorber. Although the techniques disclosed by White provide some control over contaminant concentration in the circulating solvent, the need to distill at least a portion of the solvent to prevent the build-up of high molecular weight tarry substances in the solvent increases energy requirements, adds to equipment costs, increases thermal degradation of the absorbing solvent and complicates the recovery of maleic anhydride.

SUMMARY OF THE INVENTION

Among the objects of the present invention, therefore, are the provision of an improved process for the preparation and recovery of maleic anhydride in which maleic anhydride is efficiently recovered by selectively absorbing the maleic anhydride in a suitable solvent and subsequently stripping the maleic anhydride from the resulting absorption liquor; the provision of an improved process for the preparation and recovery of maleic anhydride in which the concentration of contaminants in the circulating maleic anhydride absorbing solvent is maintained at an acceptable level; and the provision of an improved process for the preparation and recovery of maleic anhydride which prevents the build-up of polymeric tars in the circulating solvent and subsequent fouling of heat transfer surfaces without requiring that the solvent be distilled.

Briefly, therefore, the present invention is directed to a process for the preparation and recovery of maleic anhydride. The process comprises reacting a hydrocarbon having at least four carbon atoms in a straight chain with molecular oxygen in a reactor containing a vanadium-phosphorus-oxygen catalyst to produce a reaction product gas comprising maleic anhydride. After cooling, the reaction product gas is contacted with a substantially water immiscible, maleic anhydride-absorbing solvent in an absorption zone to absorb maleic anhydride from the product gas into the absorbing solvent and produce an exhaust gas substantially free of maleic anhydride and an absorption liquor comprising the absorbing solvent, maleic anhydride and contaminants comprising polymeric tars. Maleic anhydride is subsequently stripped from the absorption liquor to produce a stream comprising maleic anhydride and a regenerated absorbing solvent substantially free of maleic anhydride comprising the absorbing solvent and the contaminants. At least a portion of the regenerated absorbing solvent is contacted in an agitated extraction zone with an aqueous liquid extractant that is substantially immiscible with the regenerated absorbing solvent. Polymeric tars present in the regenerated absorbing solvent are hydrolyzed and water-soluble contaminants are transferred to the aqueous extract phase, thereby producing a mixture comprising an aqueous extract phase containing water-soluble contaminants and an organic raffinate phase comprising regenerated absorbing solvent having a reduced concentration of polymeric tars. After separating the aqueous extract and organic raffinate phases, the organic raffinate phase is recycled to the absorption zone for further absorption of maleic anhydride from the reaction product gas. In accordance with the present invention, the portion of regenerated absorbing solvent introduced into the agitated extraction zone and the conditions of temperature, agitation and contact time between the regenerated absorbing solvent and the aqueous extractant in the extraction zone are controlled such that, at an acceptable level of tars in the recirculating solvent, the rate of removal of polymeric tars by hydrolysis and extraction is substantially equivalent to the rate of introduction of tars into the absorbing solvent by absorption from the cooled product gas and generation within the solvent. In this manner, the need to distill the solvent before recycling it to the absorption zone can be effectively eliminated.

Other objects and features of this invention will be in part apparent and in part pointed out hereinafter.

DETAILED DESCRIPTION OF THE PREFERRED EMBODIMENTS

Figure 1:
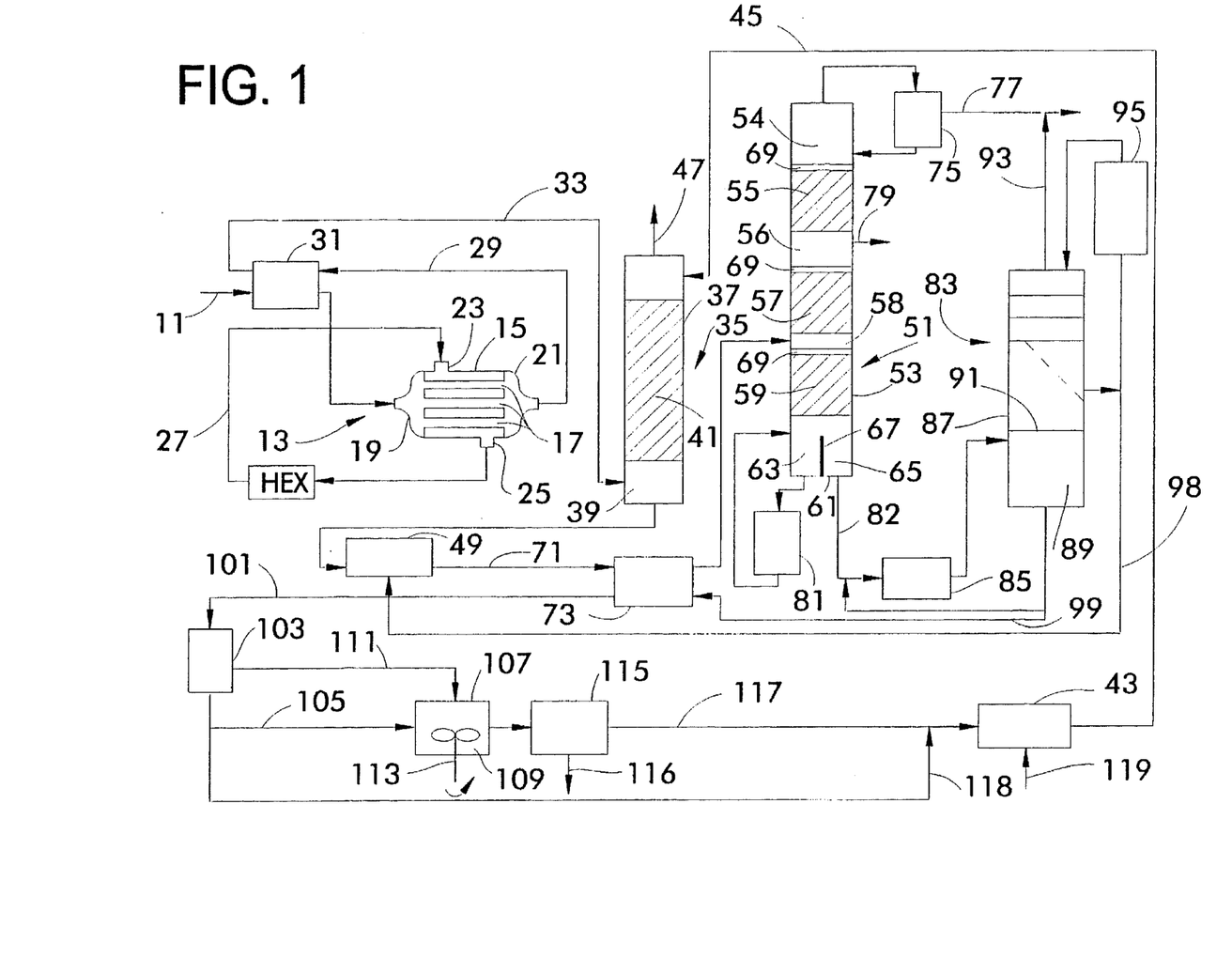
FIG. 1 is a schematic diagram of a process and apparatus for the preparation and recovery of maleic anhydride in accordance with the present invention.

A schematic diagram of the process and apparatus of the present invention is illustrated in FIG. 1. A feed gas mixture comprising molecular oxygen and a suitable hydrocarbon is introduced via line 11 into a reactor 13 containing an oxidation catalyst for the partial oxidation of the hydrocarbon to form maleic anhydride. The feed gas mixture is produced by mixing a gas containing molecular oxygen, preferably air, and a gaseous hydrocarbon feedstock. Typically, the hydrocarbon is admixed with the molecular oxygen-containing gas at a concentration of about 1.5 mole percent to about 10 mole percent hydrocarbon.

A variety of hydrocarbons can be catalytically converted to maleic anhydride. It is only necessary that the hydrocarbon feedstock contain a hydrocarbon having not less than four carbons in a straight chain (e.g., n-butane). However, the presence of hydrocarbons not having at least four carbon atoms in a straight chain (e.g., isobutane) is not harmful. Preferably, the hydrocarbon does not have more than 10 carbon atoms. In addition to n-butane, other suitable saturated hydrocarbons present in the feedstock include: pentanes, hexanes, heptanes, octanes, nonanes, decanes, and mixtures of any of these, with or without n-butane, so long as an unbranched chain having at least four carbon atoms is present in the saturated hydrocarbon molecule.

Unsaturated hydrocarbons are also suitable for catalytic conversion to maleic anhydride. Suitable unsaturated hydrocarbons may be aromatic or linear and include: benzene, butenes (1-butene and 2-butene), 1,3-butadiene, pentenes, hexenes, heptenes, octenes, nonenes, decenes, and mixtures of any of these, with or without the butenes, again, so long as the feedstock includes the requisite hydrocarbon having an unbranched chain of at least four carbons. Cyclic compounds, such as cyclopentane, cyclopentene, cyclohexane, or cyclohexene, are also satisfactory hydrocarbon feed materials for catalytic conversion to maleic anhydride. Of the aforementioned feedstocks, n-butane is the preferred saturated hydrocarbon and the butenes are the preferred unsaturated hydrocarbons, with n-butane being most preferred of all hydrocarbon feedstocks. It should be noted that the hydrocarbon feedstock need not necessarily be pure, but can be technical grade hydrocarbon.

The partial oxidation reaction of various hydrocarbons to maleic anhydride is well known to those skilled in the art. Hydrocarbons contained in the feed gas mixture are converted to maleic anhydride by contacting the feed gas mixture with an oxidation catalyst at elevated temperatures in the reactor 13. A variety of reactor configurations can be used to produce a reaction product gas comprising maleic anhydride. Both fluidized bed reactors and fixed-tube, heat-exchanger type reactors are satisfactory.

The reactor 13 shown in FIG. 1 is a fixed-tube, heat-exchanger type reactor, the details of the operation of which are well known to those skilled in the art. The reactor 13 comprises a shell 15 which encloses a plurality of tubes 17 containing a vanadium-phosphorus-oxygen catalyst. The reactor 13 further comprises an inlet means comprising an inlet head 19 for introducing the feed gas mixture into the reactor tubes 17 and an exit means comprising an exit head 21 for withdrawing the reaction product gas from the reactor. Reactor 13 can be constructed of stainless steel, carbon steel, and the like.

The catalytic oxidation of a hydrocarbon to produce maleic anhydride is a highly exothermic reaction. To remove the heat of reaction, a suitable heat transfer medium flows through the shell-side of reactor 13. Non-limiting examples of such media include Wood's metal, molten sulfur, mercury, molten lead, and eutectic salt baths. The heat transfer media enters the shell 15 through inlet 23 and, after being heated by contacting the outer surface of the reactor tubes 17, exits reactor 13 through outlet 25. The heat transfer media is subsequently cooled and recirculated via line 27 to inlet 23. A metal block reactor whereby the metal surrounding the tubes acts as a temperature regulating body can also be used.

The feed gas mixture is introduced into reactor 13 through inlet head 19 and flows through reactor tubes 17 in which it contacts the vanadium-phosphorus-oxygen catalyst. Typically, the feed gas mixture is contacted with the catalyst at a space velocity of about 100 $hr^{-1}$ to about 4,000 $hr^{-1}$ at a temperature from about 300° to about 600° C., preferably about 1450 $hr^{-1}$ and about 325° to about 425° C., to provide an excellent yield of and selectivity to maleic anhydride. Pressure is not critical to the oxidation reaction. The reaction may be conducted at atmospheric, superatmospheric, or subatmospheric pressures. For practical reasons, however, it will generally be preferred to conduct the reaction at or near atmospheric pressure. Generally, pressures from about $1.013 \times 10^2$ kPa absolute (14.7 psia, 1 atm.) to about $1.38 \times 10^2$ kPa absolute (20.0 psia) may be conveniently employed.

The reaction product gas typically contains about 0.5 to about 2 percent by volume maleic anhydride together with oxidation by-products such as CO, $CO_2$, water vapor, acrylic and acetic acids and other by-products, along with inert gases present in air when air is used as the source of molecular oxygen. It will be recognized by those skilled in the art that the type of maleic anhydride reactor, and the type and concentration of the hydrocarbon in the feed gas mixture will affect the concentrations of maleic anhydride and oxidation by-products in the reaction product gas withdrawn from the reactor.

The reaction product gas exits reactor 13 through outlet head 21 and line 29. The reaction product gas is subsequently cooled to a temperature preferably below about 200° C., but above the dew point of the water in the reaction product gas. If the product gas is cooled to a temperature below the dew point of water, maleic anhydride, or other components, these materials will accumulate on the walls of the equipment and obstruct gas flow. Generally, for a product gas containing about 1 volume percent maleic anhydride and about 10 volume percent water vapor, the product gas should be cooled to a temperature between about 60° and about 200° C., preferably between about 100° and about 150° C.

Cooling of the reaction product gas can be achieved by any suitable means. For example, in the process shown in FIG. 1, the reaction product gas flowing through line 29 is directed to a recuperative, gas-to-gas heat exchanger 31 in which heat is indirectly transferred from the reaction product gas to preheat the feed gas mixture before it is introduced into the reactor. The reaction product gas exiting heat exchanger 31 may be further cooled by passage though a waste heat boiler (not shown) to produce steam.

The cooled product gas exiting heat exchanger 31 flows via rich gas line 33 to an absorber 35 comprising means for contacting the cooled reaction product gas with a maleic anhydride-absorbing solvent in an absorption zone. As shown in FIG. 1, the absorber 35 comprises an absorber column 37 containing a sump 39 and an absorption zone 41 comprising packing material (e.g., saddles, rings etc.) for promoting gas/liquid contact and mass transfer of maleic anhydride from the gas phase to the liquid phase. Alternatively, the absorber may comprise a tray column in which gas/liquid contact is effected on the trays.

The cooled product gas is introduced through rich gas line 33 near the bottom of absorber column 37, while lean maleic anhydride-absorbing solvent from lean solvent storage tank 43 flows via lean solvent line 45 and is introduced near the top of the column. The reaction product gas and the lean solvent flow countercurrently through absorber column 37. The lower portion of absorption zone 41 acts as a direct contact condensing section, while the upper portion acts as an absorption section. Maleic anhydride is absorbed in the solvent along with a portion of the oxidation by-products (e.g., CO, $CO_2$, water, acrylic and acetic acids and polymeric tars), while the remaining oxidation by-products and inert gases in the product gas pass from the system through a vent line 47 at the top of absorber column 37 as an exhaust gas substantially free of maleic anhydride.

The absorbing solvent must have the desired solubility for maleic anhydride, a relatively low vapor pressure at the temperatures used in the process of the present invention, sufficient thermal stability to avoid excessive decomposition, and be substantially immiscible with water. Suitable absorbing solvents include dimethylbenzophenone, dichlorodiphenyloxide, hexahydrophthalates, mono alkenyl substituted succinic anhydrides having 12 to 16 carbons and dialkyl phthalates. Preferably, the solvent comprises a dialkyl phthalate compound having from two to eight carbon atoms in each alkyl chain. Suitable dialkyl phthalate compounds include: dimethyl phthalate, diethyl phthalate, dipropyl phthalate, diisopropyl phthalate, dibutyl phthalate, diisobutyl phthalate, dimethyl dihydrophthalate, diethyl dihydrophthalate, dipropyl dihydrophthalate, diisopropyl dihydrophthalate, dibutyl dihydrophthalate, diisobutyl dihydrophthalate, dimethyl tetrahydrophthalate, diethyl tetrahydrophthalate, dipropyl tetrahydrophthalate, diisopropyl tetrahydrophthalate, dibutyl tetrahydrophthalate, and diisobutyl tetrahydrophthalate, dibutyl phthalate being the most preferred maleic anhydride-absorbing solvent.

The temperature of the lean maleic anhydride-absorbing solvent introduced into the absorber column 37 can vary within wide limits. Normally, the lean solvent is introduced into the absorption step at a temperature below about 75° C., both to enhance the absorption of the maleic anhydride in the solvent and to reduce solvent losses. However, there is generally no economic advantage to using solvent at temperatures much below about 20° C., and for a reaction product gas containing about 0.2 to about 1 mole percent maleic anhydride and up to about 10 mole percent water, the lean solvent introduced into the absorbing column is preferably at a temperature between about 25° and about 45° C., and more preferably, between about 30° and about 40° C.

The ratio of lean solvent to reaction product gas introduced into the absorber column 37 can also vary within wide limits, but it is preferred for reasons of economy that the absorption liquor leaving the column contain between about 5 and about 45 weight percent maleic anhydride, more preferably between about 15 and about 20 weight percent, optimally about 17 weight percent. If the ratio of lean solvent to product gas is too large, unnecessarily large quantities of absorption liquor must be processed in subsequent steps to recover the maleic anhydride. On the other hand, if the ratio of lean solvent to product gas is too low, excessive losses of maleic anhydride may occur. Thus, it can be seen that the ratio of lean solvent to product gas depends on the amount of maleic anhydride in the product gas. For a product gas containing about 0.7 mole percent maleic anhydride and about 7 mole percent water, a ratio of lean solvent to product gas of between about 0.07 and 0.3 kilograms per cubic meter is preferred, and it is even more preferred that the ratio of lean solvent to product gas be between about 0.1 and 0.2 kilograms of solvent per cubic meter of product gas.

In addition to absorbing solvent, maleic anhydride and oxidation by-products, the absorption liquor further comprises a variety of contaminants including maleic, fumaric and phthalic acids and phthalic anhydride which are generated in the absorption and stripping loop. Maleic acid is present as a result of the hydrolysis of maleic anhydride in the absorption liquor. Maleic acid subsequently isomerizes to produce fumaric acid. Phthalic anhydride is produced as a result of an ester exchange reaction between maleic anhydride and water and, when dibutyl phthalate is used as the absorbing solvent, is also produced as a result of thermal decomposition of the solvent to phthalic anhydride and butanol. Hydrolysis of phthalic anhydride produces phthalic acid in the absorption liquor. The contaminants in the absorption liquor further include a variety of polymeric tars. These tars are typically addition polymers containing maleic anhydride, acid and ester units and, during steady state operation of the system, have a molecular weight of between about 500 and about 75,000, with an average molecular weight of about 30,000.

The absorption liquor collects in sump 39 of absorber column 37 and exits absorber column 37 from a point near the bottom of the column and flows to a rich solvent surge tank 49.

The absorption liquor is continuously stripped of maleic anhydride in a stripping step to recover crude maleic anhydride and regenerated absorbing solvent comprising the absorbing solvent and contaminants. The stripper column 51 shown in FIG. 1 comprises a suitably sized housing 53 containing a stripping zone, a rectifying zone and a pasteurization zone. Housing 53 contains a top vapor space 54, a top (pasteurizing) packed section 55, a first intermediate vapor space 56, a middle packed section 57, a second intermediate vapor space 58, a bottom packed section 59 and a divided sump 61 comprising a reboiler inlet side 63 and a spillover exit side 65 separated by a spillover baffle 67. Liquid distributors 69 (e.g., span type) are disposed on the top of each packed section 55, 57 and 59. Each of the packed sections 55, 57 and 59 contain suitable packing material such as 316 stainless steel Pall rings.

The rich absorption liquor from surge tank 49 flows via line 71 to a stripper feed preheater 73 where it is heated to a temperature of about 150° C. before being introduced into stripper column 51 at the liquid distributor 69 above the bottom packed section 59. Stripper column 51 is operated at subatmospheric pressure such that the absolute pressure within the column varies from about 25 to about 90 mm Hg in sump 61 and from about 10 to about 50 mm Hg in top vapor section 54. An absolute pressure at the bottom of the stripper column 51 above about 95 mm Hg absolute indicates a high sump temperature which could cause excessive thermal decomposition of the absorbing solvent. The temperature within the column varies between about 190° and about 245° C. in sump 61 to between about 90° and about 105° C. in the top vapor space 54. A temperature below about 87° C. at the top of stripper column 51 will not allow adequate purging of low-boilers, and a temperature above about 108° C. at the top of the column may overload the condenser.

The absorption liquor introduced into stripper column 51 is preferably above the bubble point at the prevailing pressure within the column such that maleic anhydride and lower boiling components of the absorption liquor (mostly water and acrylic acid) immediately vaporize. The vapor rising through stripper column 51, exits the top of the column and enters stripper condenser 75 (e.g., a vertical down-flow shell and tube heat exchanger). The vapor is cooled to about 66° C. to produce a condensate. The sump on condenser 75 is one-sided and acts as a reflux chamber. The temperature of condensate leaving the sump is preferably maintained between about 60° and about 90° C., by throttling the flow of cooling water leaving the shell side of condenser 75. Uncondensed components of the vapor exit stripper condenser 75 via line 77. All the condensate formed in stripper condenser 75 is returned to stripper column 51 as reflux and enters the column at the liquid distributor 69 above the top packed section 55.

A liquid sidedraw of crude maleic anhydride is continuously removed from stripper column 51 via a chimney tray liquid trap below the top packed section 55 and line 79. The crude product is forwarded to a maleic anhydride purification stage (not shown).

The liquid phase flows downward from the column feed inlet through bottom packed section 59 and is directed to the reboiler inlet side 63 of sump 61. Liquid from this side of the sump circulates through a stripper reboiler 81 which may be of the thermosiphon-type comprising a vertical shell and tube heat exchanger. Steam flow within stripper reboiler 81 is controlled to maintain a minimum liquid temperature between about 210° and about 246° C. in the spillover exit side 65 of sump 61. However, this temperature set point may need periodic adjustment based on the composition of the stripped solvent. Liquid returning from reboiler 81 is introduced into sump 61 where some of the heated liquid is vaporized in the reduced pressure environment and flows upward through bottom packed section 59, while the remaining liquid portion returns to the reboiler inlet side 63 of sump 61. At steady state, the reboiler inlet side 63 of sump 61 is filled with liquid which overflows spillover baffle 67 into the spillover exit side 65 of the sump as stripper bottoms.

As shown in FIG. 1, stripper bottoms from sump 61 is pumped forward via line 82 to an afterflasher 83 for further removal of maleic anhydride. The use of an afterflasher is not critical to the present invention, but is preferred to increase the yield of maleic anhydride. The stripper bottoms passes through a stripper bottoms heater 85 which acts as a forced-circulation suppressed-boiling reboiler. The stripper bottoms heater 85 may be a fixed shell and tube heat exchanger which uses high pressure steam on the shell side as a heat source.

Afterflasher 83 comprises a vessel 87 containing a sump 89 and has an impingement baffle 91 mounted therein at a suitable distance from the bottom of the unit. Heated stripper bottoms exiting heater 85 is introduced into afterflasher 83 and flash vaporizes against impingement baffle 91, while nonvaporized liquid collects in sump 89. The top section of afterflasher 83 contains several spaced shower-deck trays with a bucket tray below. Vapor flowing up into the top section of afterflasher 83 is cooled and partially condensed by contact with cooled condensate in the shower deck trays, the condensate being collected in the bucket tray and removed from the bucket tray through a side exit of the column. The fraction of the vapor which is not condensed exits afterflasher 83 via line 93. This vapor is combined with the uncondensed components of the vapor exiting stripper condenser 75 via line 77. If desired, this vapor may be further treated to recover additional maleic anhydride before being discharged from the system.

Condensate withdrawn from the side exit of afterflasher 83 is divided into two streams. One stream is cooled in afterflasher cooler 95 and recirculated back to the top section of afterflasher 83 to serve as the cooling and condensing medium therein. The remainder of the afterflasher condensate flows via line 98 to rich solvent surge tank 49.

The temperature in the afterflasher bottoms is controlled by controlling steam flow to stripper bottoms heater 85. The temperature in the afterflasher bottoms and the pressure in the afterflasher are controlled such that the afterflasher bottoms is substantially free of maleic anhydride. For example, the concentration of maleic anhydride in the afterflasher bottoms is preferably maintained below about 0.3 weight percent, more preferably below about 0.15 weight percent. At an afterflasher operating pressure of about 35 mm Hg absolute, a temperature in the afterflasher bottoms of between about 200° and about 216° C. corresponds to a maleic anhydride concentration in the afterflasher bottoms of about 0.3 weight percent.

Fumaric acid in the stripper bottoms is vaporized and condenses in the shower-deck condenser of afterflasher 83. Were it not further diluted, the resulting afterflasher condensate would contain more fumaric acid than could remain in solution, resulting in plugging of process lines and fouling of heat transfer surfaces. Dilution of the afterflasher condensate may be accomplished by injecting rich absorption liquor (low fumaric acid concentration) from the absorber column sump 39 and/or rich solvent surge tank 49 into the inlet of the afterflasher cooler 95 which greatly increases the condensate blowdown rate from afterflasher 83 and thereby keeps the fumaric acid in solution.

A second reason for feeding rich absorption liquor to the afterflasher cooler 95 is to expose the liquor to vacuum prior to storage in rich solvent tank 49. This flashes off about one-half of the water present in the rich absorption liquor, reducing the formation of maleic acid (and subsequent isomerization to fumaric acid) by approximately one-half. Typically, the flow of rich absorption liquor used in diluting the afterflasher condensate represents about 70 percent of the feed to stripper 51 on a volume basis.

Regenerated absorbing solvent comprising solvent, trace amounts of maleic anhydride and contaminants (e.g., acrylic, maleic, fumaric and phthalic acids, phthalic anhydride and polymeric tars) collects in sump 89 of afterflasher 83. A portion of the regenerated absorbing solvent is recirculated through stripper bottoms heater 85 while the remainder is directed via line 99 to stripper feed preheater 73 and used to preheat the rich absorption liquor fed to stripper column 51. The regenerated absorbing solvent exiting stripper feed preheater 73 is then forwarded via line 101 to the regenerated absorbing solvent handling area.

In accordance with the process of the present invention, the regenerated absorbing solvent is further treated to remove various contaminants before recycling the solvent for use again in the absorption step as lean absorbing solvent.

Regenerated absorbing solvent flows from stripper feed preheater 73 via line 101 to cooler 103 where it is further cooled. At least a portion of the cooled, regenerated absorbing solvent is then fed via line 105 to an extractor 107. Typically, a slip stream constituting from about 15 to about 75 percent of the total flow of regenerated absorbing solvent exiting cooler 103 is fed to extractor 107. In the extractor, the flow of regenerated solvent is contacted with an aqueous liquid extractant in an agitated extraction zone 109. The aqueous liquid extractant is substantially immiscible with the regenerated absorbing solvent and is introduced into extractor 107 via line 111. Preferably, the aqueous liquid extractant is deionized water.

As a result of contacting the regenerated absorbing solvent with the aqueous extractant, water-soluble contaminants (e.g., acrylic, maleic, fumaric and phthalic acids) contained in the regenerated solvent are transferred to the aqueous extractant and a two-phase mixture comprising an aqueous extract phase and an organic raffinate phase is produced. The organic raffinate phase contains regenerated absorbing solvent in which the concentration of contaminants has been reduced.

Extractor 107 may comprise a suitably-sized pressure vessel having an inlet for the regenerated solvent, an inlet for the aqueous liquid extractant and an outlet for withdrawing the two phase mixture comprising the aqueous extract phase and the organic raffinate phase from the extractor. Extractor 107 further comprises means for agitating the mixture of the aqueous and organic phases within the extraction zone to promote intimate turbulent contact between the phases and mass transfer of water-soluble contaminants from the regenerated solvent to the aqueous phase. As shown in FIG. 1, a suitable agitating means may comprise a propeller 113.

Generally, the temperature in extraction zone 109 is maintained at from about 50° to about 80° C., preferably from about 60° to about 70° C. Temperature control in the extraction zone may be achieved by controlling the temperature of the regenerated solvent and the aqueous extractant introduced into the extraction zone. The temperature of the regenerated solvent introduced into extractor 107 is controlled by operation of cooler 103. If necessary, the aqueous extractant introduced into extractor 107 may be preheated. Preferably, both the regenerated solvent and the aqueous extractant are introduced into extractor 107 at a temperature essentially equivalent to the temperature desired in extraction zone 109.

The agitation means is preferably operated so as to impart from about $3 \times 10^{-4}$ to about $2 \times 10^{-3}$ horsepower per gallon of the mixture of the aqueous and organic phases in extraction zone 109.

The ratio of the volumetric proportions of aqueous extractant to regenerated absorbing solvent charged to the extraction zone is from about 1:1 to about 1:10, preferably from about 1:4 to about 1:6. The ratio of volumetric proportions of aqueous extractant to regenerated absorbing solvent charged to the extraction zone is controlled by the relative flowrates through lines 111 and 105, respectively.

It has been found that adequate removal of water-soluble contaminants contained in the partially regenerated solvent stream can be achieved with a contact time of between about 5 and about 10 minutes in a continuous back mixed extraction vessel under the temperature and agitation conditions discussed above. Thus, the extractor may be sized, and the flow rates of the partially regenerated solvent and aqueous extractant feed stream may be controlled, to provide a 5 to 10 minute residence time in the extraction tank 107. Moreover, water-soluble contaminants are adequately removed from the circulating solvent under the above conditions by passing only a slip stream of about 15 to about 75 percent of the total flow of regenerated solvent exiting cooler 103 through the extractor.

The binary mixture of the aqueous extract phase and the organic raffinate phase exiting extractor 107 passes to a liquid-liquid separator 115 to separate the two phases. Depending upon the density differential between the two phases, a variety of suitable separators may be employed, including sieve plate gravity separators and centrifugal contactors. Centrifugal contactors are simple and effective liquid-liquid separators, comprising a rotor and shaft assembly. Mounted within the rotor are a number of concentric, perforated cylindrical elements. The mixture of the aqueous extract and organic raffinate phases is introduced into the contactor at the appropriate radial position within the spinning rotor to provide forces for the initial separation and the clarifying volumes to capture lingering entrainment. The shaft is "up" and the rotor is "down" under the simulated gravity of the spinning rotor assembly so that the concentric perforated elements mounted within the rotor perform the same function as horizontal sieve plates in a gravity separator. As the rotor spins, the more dense organic raffinate phase accumulates on the inner surface of the perforated cylindrical elements as they rotate on the shaft. Droplets of the organic phase pass through the perforations in the elements, displacing an equal volume of the less dense aqueous phase back through the same perforations. Thus, the organic phase flows outward toward the rim of the rotor and the aqueous phase flows toward the shaft, allowing the two phases to be separated into two well-defined phases. Suitable centrifugal contactors include those sold under the Podbielniak trademark available from Baker Perkins Inc., Chemical Machinery Division, Saginaw, Mich., 48601.

The separated aqueous extract phase containing the water-soluble contaminants transferred from the regenerated absorbing solvent is discharged from the system as waste via line 116, while the separated organic raffinate phase exits separator 115 via line 117 and is combined with any solvent that was bypassed around extractor 107 via line 118. The combined stream is then passed to lean solvent storage tank 43. Make-up fresh solvent is introduced into tank 43 via line 119 as needed to compensate for system losses. Lean maleic anhydride absorbing solvent is then recycled to absorption zone 41 of absorber 35 to absorb maleic anhydride from the reaction product gas.

Polymeric tars present in the regenerated absorbing solvent fed to extractor 107 are substantially insoluble in water and, as a result, are not readily transferred to the aqueous extract phase during the extraction step under the conditions as described above. Therefore, in order to prevent the undesirable build-up of tars in the circulating absorbing solvent, the organic raffinate phase exiting separator 115 may be distilled to separate polymeric tars before passing the organic raffinate phase to lean solvent storage tank 43. Alternatively, a slip stream of the lean absorption solvent flowing in line 45 may be distilled before the solvent is introduced into absorption zone 41 of absorber 35.

In operation under the conditions outlined above, maleic anhydride and phthalic anhydride contained in the solvent phase are substantially hydrolyzed to the corresponding acids, which are transferred to the aqueous phase along with other contaminants such as fumaric and acrylic acid. It has further been observed that a small fraction of the polymeric tars are also hydrolyzed and transferred to the aqueous phase. However, the extent of hydrolysis and extraction of tars is minimal under these conditions, and insufficient to maintain the tars at an acceptable level in the circulating solvent stream. If removed only by the limited hydrolysis and extraction observed in the extraction step, the tars would build up to levels which would cause severe fouling of heat transfer surfaces and other problems in the maleic recovery process. In fact, the rate of removal is so minimal that, if tars were removed only by extraction under the above conditions, tar accumulation would increase by autocatalysis at a progressively accelerating rate, essentially without limit. Accordingly, it has been deemed necessary to remove such tars by distillation of the lean absorbing solvent, as described hereinabove.

Further in accordance with the invention, however, it has now been discovered that contact of the partially regenerated solvent with an aqueous extractant can been carried out under modified conditions which are effective to hydrolyze and extract a very substantial fraction of the tars. In particular, it has been found that, by use of a more severe combination of temperature, agitation and contact time than that described above for extraction alone, the tars may be substantially hydrolyzed to a form which has substantial water solubility. The hydrolyzed tars are transferred in substantial part to the aqueous phase and removed from the process. More particularly, it has been found that, at an acceptable steady state level of tars in the circulating absorbing solvent, e.g., 0.6 to 3.5 percent by weight, the rate of removal of polymeric tars by hydrolysis and extraction is substantially equivalent to the rate of introduction of tars into the absorbing solvent by absorption from the cooled product gas and generation within the solvent at heat transfer surfaces, etc. In this manner, the steady state concentration of polymeric tars can be maintained at an acceptable level without any need for distillation of the lean absorbing solvent. Although the present invention is not limited to a particular theory, it is believed that hydrolysis of the tars involves hydrolyzing the anhydride units present in the tars to form a more water-soluble polymer containing more free carboxylic acids.

In accordance with this especially preferred embodiment of the invention, the conditions of the extraction step are carefully controlled in order to more effectively hydrolyze polymeric tars in the regenerated solvent introduced into extraction zone 109 and transfer water-soluble contaminants to the aqueous phase such that the rate of tar removal through the discarded aqueous waste may be matched with or exceed the rate of tar generation in the circulating solvent. Preferably, the ratio of aqueous extractant to regenerated solvent introduced into extraction zone 109, the portion of regenerated absorbing solvent introduced into the agitated extraction zone, extraction zone temperature and agitation and contact time between solvent and extractant in the extraction zone are controlled to hydrolyze and remove tars at a rate such that, without distillation of the regenerated absorbing solvent, the steady state concentration of polymeric tars in the organic raffinate phase recycled to the absorption zone does not exceed about 4 weight percent, more preferably about 2 weight percent.

By increasing the proportion of the regenerated solvent exiting cooler 103 and diverted to extraction zone 109, a larger proportion of the polymeric tars present in the circulating solvent may be contacted with the aqueous liquid extractant, hydrolyzed and removed. However, to minimize the requisite capacity, capital cost and operating cost of the liquid/liquid separation equipment, it is particularly preferred that tars be hydrolyzed and removed at a rate sufficient to maintain the tar concentration at the aforesaid steady state levels while diverting to the hydrolysis system a slip stream of no more than about 15 to about 75 percent, preferably about 35 to about 60 percent, of the regenerated solvent exiting cooler 103.

To achieve the requisite steady state tar levels by treatment of a 15 to 75 percent slip stream of regenerated solvent, it is typically necessary to hydrolyze and remove at least about 6.5 percent by weight, more preferably at least about 13 percent by weight, of the tars in the stream entering the hydrolysis reactor, i.e., extractor 107. Since each of temperature, agitation and contact time affect the rate of hydrolysis, a variety of combinations of these variables may be selected for the tar hydrolysis process. Generally, the temperature of hydrolysis should be between about 60° and about 80° C., preferably between about 65° and about 75° C. The contact time is preferably substantially longer than described hereinabove. Depending on temperature and agitation conditions, contact time should ordinarily be at least about 15 minutes, more preferably at least about 30 minutes, most preferably in the range of between about 45 and about 120 minutes. The ratio of extractant to regenerated solvent introduced into the extraction zone 109 for achieving increased tar hydrolysis is essentially the same as described above.

Higher extraction zone temperatures, increased extraction zone agitation and longer contact times in the extraction zone are each believed to independently increase the proportion of the tars present in the regenerated solvent that are hydrolyzed and transferred to the aqueous phase. However, because increased severity of the combination of temperature, agitation, and contact time also tends to promote emulsification, the combination selected must be sufficient to hydrolyze tars at an adequate rate, without formation of a stable emulsion. With respect to both tar hydrolysis and emulsion formation, these three operating variables have been found to be interrelated, and apparently to interact. Thus: (1) the maximum value of any of these parameters which can be tolerated without emulsion formation decreases as the values of the other parameters increase; and (2) the beneficial effect of a given value of any of these parameters increases as the values of the other parameters increase. Fortunately, it has been discovered that a window of operation exists in which effective tar hydrolysis and extraction are realized without formation of an emulsion, or at least without formation of an emulsion that cannot be broken in a suitable liquid/liquid separator.

This window of operation includes: (1) contacting the regenerated absorbing solvent with the aqueous extractant in extraction zone 109 at a temperature between about 60° and about 80° C., preferably at a temperature between about 65° and about 75° C.; (2) operating the agitation means so as to impart from about $3 \times 10^{-4}$ to about $2 \times 10^{-3}$ horsepower per gallon of the mixture of the aqueous and organic phases in extraction zone 109; and (3) contacting the regenerated solvent and the aqueous liquid extractant for at least about 15 minutes, more preferably for at least about 30 minutes, but no greater than about 120 minutes. While more aggressive temperature and agitation may be used with a somewhat more modest residence time, these variables, especially agitation, entail a greater risk of stable emulsion formation. It has been found that the conflicting goals of tar hydrolysis and clean phase separation are most effectively achieved under the conditions specified above.

The present invention is illustrated by the following examples which are merely for the purpose of illustration and are not to be regarded as limiting the scope of the invention or manner in which it may be practiced.

EXAMPLE 1

A mock regenerated absorbing solvent representative of the solvent exiting the stripper was prepared comprising a mixture of dibutyl phthalate (97.53 weight percent) and polymeric tars (2.47 weight percent). This mixture (2000 ml) was charged to a suitably sized vessel equipped with a paddle agitator. The contents of the vessel were heated to 60° C., while deionized water (500 ml) was heated separately to approximately the same temperature. With the paddle agitator operating at 300 rpm, the water was added to the contents of the vessel. After 15 minutes of contact time between the water and the regenerated absorbing solvent, a sample of the mixture in the stirred vessel was withdrawn and fed to a lab-scale, centrifugal contactor to separate the aqueous extract and organic raffinate phases. Further samples of the mixture in the vessel were withdrawn after 30, 60, and 120 minutes of contact time, and likewise fed to the centrifugal contactor to separate the aqueous and organic phases. The separated aqueous phases were then analyzed to determine the hydrolyzed tar content thereof. The above-described procedure was then repeated in a second run. Summarized below in Table I is the hydrolyzed tar content for each of the aqueous phases of the mixtures withdrawn from the vessel after varying contact times.

TABLE I

| Contact time | Tar Content of Aqueous Phase (weight %) | |
|---|---|---|
| (minutes) | run #1 | run #2 |
| 15 | 0.306 | 0.255 |
| 30 | 0.325 | 0.276 |
| 60 | 0.364 | 0.401 |
| 120 | 0.541 | 0.599 |

EXAMPLE 2

An experiment was conducted to determine the effects of temperature, contact time and agitation on the hydrolytic extraction of polymeric tars contained in a mock regenerated absorption solvent.

A mixture intended to be representative regenerated absorption solvent exiting the stripping column was prepared comprising dibutyl phthalate (97.55 percent by weight) and polymeric tars (2.45 percent by weight). The regenerated absorption solvent was charged to a 3-liter round bottom, 3-necked flask fitted with a paddle agitator driven by a variable speed motor. The flask was then placed on a variable temperature heating mantle and heated to the desired temperature. In a separate vessel, a quantity of deionized water equal to one fourth of the volume of regenerated absorption solvent charged to the 3-liter flask was heated to the same temperature as the mixture in the flask. The heated water was then combined with the heated solvent mixture in the flask and the paddle agitator was started at the desired speed. After a predetermined contact time had elapsed, a sample of the mixture in the stirred flask was withdrawn and fed to a lab-scale, centrifugal contactor to separate the aqueous extract and organic raffinate phases. The separated aqueous phases was then analyzed to determine the hydrolyzed tar content thereof. The above-described procedure was repeated several times, varying the temperature, contact time and rotation speed of the paddle agitator.

Summarized below in Table II is the hydrolyzed tar content for each of the aqueous phases of the mixtures withdrawn from the flask under varying conditions with respect to temperature, contact time and agitation. Also summarized is the condition of the mixture of the aqueous and organic phases with respect to emulsion formation. Severe emulsion formation indicates that the mixture could not be phase separated without large solvent losses and, therefore, the associated conditions would be generally less preferred in the practice of the present invention. Moderate and slight emulsion formation and the absence of an emulsion indicates that phase separation could be achieved without large solvent losses and the associated conditions would be generally more preferred in the practice of the present invention.

TABLE II

| Run | Temperature (°C.) | Contact Time (Min.) | RPM | Tar Content Aqueous Phase (weight %) | Emulsion Formation |
|---|---|---|---|---|---|
| 1 | 80 | 30 | 600 | 1.07 | None |
| 2 | 60 | 30 | 400 | 0.51 | None |
| 3 | 70 | 75 | 500 | 1.81 | Moderate |
| 4 | 80 | 120 | 400 | 2.29 | Severe |
| 5 | 70 | 75 | 500 | 1.13 | Moderate |
| 6 | 70 | 75 | 500 | 1.03 | Moderate |
| 7 | 60 | 120 | 600 | 1.18 | Severe |
| 8 | 60 | 120 | 400 | 0.98 | Moderate |
| 9 | 80 | 30 | 400 | 0.82 | Slight |
| 10 | 80 | 120 | 600 | 4.96 | Severe |
| 11 | 50 | 30 | 600 | 0.33 | None |

In view of the above, it will be seen that the several objects of the invention are achieved.

As various changes could be made in the above-described invention without departing from its scope, it is intended that all matter contained in the above description be interpreted as illustrative and not in a limiting sense.

What is claimed:

1. A process for the preparation and recovery of maleic anhydride comprising:

reacting a hydrocarbon having at least four carbon atoms in a straight chain with molecular oxygen in a reactor containing a vanadium-phosphorus-oxygen catalyst for the catalytic oxidation of the hydrocarbon to maleic anhydride to produce a reaction product gas comprising maleic anhydride;

cooling said reaction product gas;

contacting said cooled product gas with a substantially water immiscible, maleic anhydride-absorbing solvent in an absorption zone, thereby absorbing maleic anhydride from said product gas into said absorbing solvent, and producing an exhaust gas substantially free of maleic anhydride and an absorption liquor comprising said absorbing solvent, maleic anhydride and contaminants comprising polymeric tars;

stripping maleic anhydride from the absorption liquor to produce a stream comprising maleic anhydride and a regenerated absorbing solvent substantially free of maleic anhydride comprising said absorbing solvent and said contaminants;

contacting at least a portion of said regenerated absorbing solvent in an agitated extraction zone with an aqueous liquid extractant that is substantially immiscible with said regenerated absorbing solvent to hydrolyze polymeric tars present in said regenerated absorbing solvent and transfer water-soluble contaminants to said aqueous extract phase, thereby producing a mixture comprising an aqueous extract phase containing water-soluble contaminants and an organic raffinate phase comprising regenerated absorbing solvent having a reduced concentration of polymeric tars;

separating said aqueous extract and said organic raffinate phases; and recycling said organic raffinate phase to said absorption zone for absorption of maleic anhydride from said reaction product gas;

the portion of regenerated absorbing solvent introduced into said agitated extraction zone and the conditions of temperature, agitation and contact time between said regenerated absorbing solvent and said aqueous extractant in said extraction zone being controlled such that a stable emulsion is not formed in said extraction zone and, at an acceptable level of tars in the recirculating solvent, the rate of removal of polymeric tars by hydrolysis and extraction is substantially equivalent to the rate of introduction of tars into the absorbing solvent by absorption from said cooled product gas and generation within said solvent.

2. The process as set forth in claim 1 wherein, at a polymeric tar concentration of between about 0.6 and about 3.5 percent by weight in the regenerated absorbing solvent stream entering the extraction zone, at least about 6.5 percent by weight of the tars in said regenerated solvent stream are removed by hydrolysis and transferred to the aqueous phase.

3. The process as set forth in claim 1 wherein the concentration of polymeric tars in said organic raffinate phase recycled to said absorption zone does not exceed about 4 weight percent.

4. The process as set forth in claim 3 wherein said concentration of polymeric tars in said organic raffinate phase recycled to said absorption zone is maintained by contacting a slip stream comprising from about 15 to about 75 percent of said regenerated absorbing solvent with said aqueous extractant in said extraction zone, and blending the organic raffinate from said extraction with the remainder of said regenerated absorbing solvent for recycle to said absorption zone.

5. The process as set forth in claim 1 wherein said aqueous liquid extractant contacted with said regenerated absorbing solvent in said extraction zone is deionized water.

6. The process as set forth in claim 5 wherein said regenerated absorbing solvent is contacted with deionized water in said extraction zone at a temperature between about 60° and about 80° C.

7. The process as set forth in claim 6 wherein the ratio of volumetric proportions of deionized water to regenerated absorbing solvent charged to said extraction zone is from about 1:1 to about 1:10.

8. The process as set forth in claim 7 wherein the ratio of volumetric proportions of deionized water to regenerated absorbing solvent charged to said extraction zone is from about 1:4 to about 1:6.

9. The process as set forth in claim 8 wherein said regenerated absorbing solvent and said aqueous liquid extractant are contacted in said extraction zone for at least about 30 minutes.

10. The process as set forth in claim 6 wherein the deionized water charged to said extraction zone is preheated to approximately the temperature maintained in said extraction zone.

11. The process as set forth in claim 1 wherein said maleic anhydride-absorbing solvent comprises a compound selected from the group consisting of dimethyl phthalate, diethyl phthalate, dipropyl phthalate, diisopropyl phthalate, dibutyl phthalate, diisobutyl phthalate, dimethyl dihydrophthalate, diethyl dihydrophthalate, dipropyl dihydrophthalate, diisopropyl dihydrophthalate, dibutyl dihydrophthalate, diisobutyl dihydrophthalate, dimethyl tetrahydrophthalate, diethyl tetrahydrophthalate, dipropyl tetrahydrophthalate, diisopropyl tetrahydrophthalate, dibutyl tetrahydrophthalate, diisobutyl tetrahydrophthalate, dimethylbenzophenone, dichlorodiphenyloxide, hexahydrophthalates and mono alkenyl substituted succinic anhydrides having 12 to 16 carbons.

12. The process as set forth in claim 11 wherein said maleic anhydride-absorbing solvent comprises dibutyl phthalate.

13. The process as set forth in claim 12 wherein the aqueous extract and organic raffinate phases are separated using a centrifugal contactor.

14. The process as set forth in claim 1 wherein said hydrocarbon comprises n-butane.

15. The process as set forth in claim 1 wherein said regenerated absorbing solvent is contacted with said aqueous liquid extractant in said agitated extraction zone at a temperature between about 60° and about 80° C. for at least about 15 minutes.

16. The process as set forth in claim 15 wherein said regenerated absorbing solvent is contacted with said aqueous liquid extractant in said agitated extraction zone for at least about 30 minutes.

17. The process as set forth in claim 16 wherein said regenerated absorbing solvent is contacted with said aqueous liquid extractant in said agitated extraction zone for between about 45 and about 120 minutes.

18. The process as set forth in claim 15 wherein the mixture of said organic raffinate and aqueous extract phases in said extraction zone is agitated with a power input of between about $3\times10^{-4}$ and about $2\times10^{-3}$ horsepower per gallon of mixture.

19. A process for the preparation and recovery of maleic anhydride comprising:

reacting a hydrocarbon having at least four carbon atoms in a straight chain with molecular oxygen in a reactor containing a vanadium-phosphorus-oxygen catalyst for the catalytic oxidation of the hydrocarbon to maleic anhydride to produce a reaction product gas comprising maleic anhydride;

cooling said reaction product gas;

contacting said cooled product gas with a substantially water immiscible, maleic anhydride-absorbing solvent in an absorption zone, thereby absorbing maleic anhydride from said product gas into said absorbing solvent, and producing an exhaust gas substantially free of maleic anhydride and an absorption liquor comprising said absorbing solvent, maleic anhydride and contaminants comprising polymeric tars;

stripping maleic anhydride from the absorption liquor to produce a stream comprising maleic anhydride and a regenerated absorbing solvent substantially free of maleic anhydride comprising said absorbing solvent and said contaminants;

contacting at least a portion of said regenerated absorbing solvent in an agitated extraction zone with an aqueous liquid extractant that is substantially immiscible with said regenerated absorbing solvent to hydrolyze polymeric tars present in said regenerated absorbing solvent and transfer water-soluble contaminants to said aqueous extract phase, thereby producing a mixture comprising an aqueous extract phase containing water-soluble contaminants and an organic raffinate phase comprising regenerated absorbing solvent having a reduced concentration of polymeric tars;

separating said aqueous extract and said organic raffinate phases; and recycling said organic raffinate phase to said absorption zone for absorption of maleic anhydride from said reaction product gas, said organic raffinate phase recycled to said absorption zone not having been distilled for removal of polymeric tars;

the portion of regenerated absorbing solvent introduced into said agitated extraction zone and the conditions of temperature, agitation and contact time between said regenerated absorbing solvent and said aqueous extractant in said extraction zone being controlled such that, at an acceptable level of tars in the recirculating solvent, the rate of removal of polymeric tars by hydrolysis and extraction is substantially equivalent to the rate of introduction of tars into the absorbing solvent by absorption from said cooled product gas and generation within said solvent.

20. A process for the preparation and recovery of maleic anhydride comprising:

reacting a hydrocarbon having at least four carbon atoms in a straight chain with molecular oxygen in a reactor containing a vanadium-phosphorus-oxygen catalyst for the catalytic oxidation of the hydrocarbon to maleic anhydride to produce a reaction product gas comprising maleic anhydride;

cooling said reaction product gas;

contacting said cooled product gas with a substantially water immiscible, maleic anhydride-absorbing solvent in an absorption zone, thereby absorbing maleic anhydride from said product gas into said absorbing solvent, and producing an exhaust gas substantially free of maleic anhydride and an absorption liquor comprising said absorbing solvent, maleic anhydride and contaminants comprising polymeric tars;

stripping maleic anhydride from the absorption liquor to produce a stream comprising maleic anhydride and a regenerated absorbing solvent substantially free of maleic anhydride comprising said absorbing solvent and said contaminants;

contacting from about 15 to about 75 percent of said regenerated absorbing solvent in an agitated extraction zone with an aqueous liquid extractant that is substantially immiscible with said regenerated absorbing solvent to hydrolyze polymeric tars present in said regenerated absorbing solvent and transfer water-soluble contaminants to said aqueous extract phase, thereby producing a mixture comprising an aqueous extract phase containing water-soluble contaminants and an organic raffinate phase comprising regenerated absorbing solvent having a reduced concentration of polymeric tars, said extraction zone being maintained at a temperature between about 60° and about 80° C., said mixture of said organic raffinate and said aqueous extract phases in said extraction zone being agitated with a power input of between about $3 \times 10^{-4}$ and about $2 \times 10^{-3}$ horsepower per gallon of said mixture and said regenerated absorbing solvent being contacted with said aqueous extractant for at least about 15 minutes;

separating said aqueous extract and said organic raffinate phases; and recycling said organic raffinate phase to said absorption zone for absorption of maleic anhydride from said reaction product gas;

the portion of regenerated absorbing solvent introduced into said agitated extraction zone and the conditions of temperature, agitation and contact time between said regenerated absorbing solvent and said aqueous extractant in said extraction zone being controlled such that a stable emulsion is not formed in said extraction zone and, at an acceptable level of tars in the recirculating solvent, the rate of removal of polymeric tars by hydrolysis and extraction is substantially equivalent to the rate of introduction of tars into the absorbing solvent by absorption from said cooled product gas and generation within said solvent.

21. A process for the preparation and recovery of maleic anhydride comprising:

reacting a hydrocarbon having at least four carbon atoms in a straight chain with molecular oxygen in a reactor containing a vanadium-phosphorus-oxygen catalyst for the catalytic oxidation of the hydrocarbon to maleic anhydride to produce a reaction product gas comprising maleic anhydride;

cooling said reaction product gas;

contacting said cooled product gas with a substantially water immiscible, maleic anhydride-absorbing solvent in an absorption zone, thereby absorbing maleic anhydride from said product gas into said absorbing solvent, and producing an exhaust gas substantially free of maleic anhydride and an absorption liquor comprising said absorbing solvent, maleic anhydride and contaminants comprising polymeric tars;

stripping maleic anhydride from the absorption liquor to produce a stream comprising maleic anhydride and a regenerated absorbing solvent substantially free of maleic anhydride comprising said absorbing solvent and said contaminants;

contacting from about 15 to about 75 percent of said regenerated absorbing solvent in an agitated extraction zone with an aqueous liquid extractant that is substantially immiscible with said regenerated absorbing solvent to hydrolyze polymeric tars present in said regenerated absorbing solvent and transfer water-soluble contaminants to said aqueous extract phase, thereby producing a mixture comprising an aqueous extract phase containing water-soluble contaminants and an organic raffinate phase comprising regenerated absorbing solvent having a reduced concentration of polymeric tars;

separating said aqueous extract and said organic raffinate phases; and recycling said organic raffinate phase to said absorption zone for absorption of maleic anhydride from said reaction product gas;

the conditions of temperature, agitation and contact time between said regenerated absorbing solvent and said aqueous extractant in said extraction zone being controlled such that, at a polymeric tar concentration of between about 0.6 and about 3.5 percent by weight in the regenerated absorbing solvent stream entering said extraction zone, at least about 6.5 percent by weight of the tars in the regenerated solvent stream entering said extraction zone are transferred to said aqueous extract phase.

\* \* \* \* \*